(12) United States Patent
Koops et al.

(10) Patent No.: US 11,439,753 B2
(45) Date of Patent: Sep. 13, 2022

(54) APPARATUS FOR REGULATING THE CONCENTRATION OF GLUCOSE IN THE BLOOD OF A PERSON

(71) Applicant: Inreda Diabetic B.V., Goor (NL)

(72) Inventors: Robin Koops, Goor (NL); Gijs Benno Westen, Bornerbroek (NL)

(73) Assignee: Inreda Diabetic B.V., Goor (NL)

( * ) Notice: Subject to any disclaimer, the term of this patent is extended or adjusted under 35 U.S.C. 154(b) by 548 days.

(21) Appl. No.: 16/464,883

(22) PCT Filed: Nov. 29, 2017

(86) PCT No.: PCT/EP2017/080830
§ 371 (c)(1),
(2) Date: May 29, 2019

(87) PCT Pub. No.: WO2018/099976
PCT Pub. Date: Jun. 7, 2018

(65) Prior Publication Data
US 2020/0093989 A1 Mar. 26, 2020

(30) Foreign Application Priority Data
Nov. 30, 2016 (EP) .................................. 16201413

(51) Int. Cl.
*G08B 21/04* (2006.01)
*A61M 5/172* (2006.01)
*A61B 5/00* (2006.01)

(52) U.S. Cl.
CPC ......... *A61M 5/1723* (2013.01); *A61B 5/4809* (2013.01); *A61M 2205/18* (2013.01);
(Continued)

(58) Field of Classification Search
CPC ............ A61B 5/14532; A61B 5/14865; A61B 5/1495; A61B 5/6898; A61B 5/742;
(Continued)

(56) References Cited

U.S. PATENT DOCUMENTS

| 4,403,984 A | 9/1983 | Ash et al. |
| 5,474,552 A * | 12/1995 | Palti .................... A61M 5/1723 604/67 |

(Continued)

FOREIGN PATENT DOCUMENTS

| EP | 1703839 B1 | 2/2012 |
| WO | 2007049961 A2 | 5/2007 |
| WO | 2009081262 A1 | 7/2009 |

*Primary Examiner* — Daniel Previl
(74) *Attorney, Agent, or Firm* — The Webb Law Firm (57) ABSTRACT

An apparatus for regulating the concentration of glucose in the blood of a person includes: at least one glucose sensor that is arranged to measure the glucose concentration of the person, for example in the interstitial fluid or blood; a pump for selectively introducing at least one substance influencing the blood glucose levels into the body of the person, for instance by at least one cannula or catheter to be inserted into the body of said person, and a control for controlling said at least one substance influencing the blood glucose levels to be introduced to the person based on data received from said glucose sensor. Said apparatus includes at least one further sensor that is arranged to monitor a further characteristic of the person. The at least one further sensor may include an accelerometer, a heart rate sensor, a temperature sensor, a pH sensor, a ketone sensor, a GPS receiver, and/or a skin resistance sensor.

10 Claims, 5 Drawing Sheets

(52) U.S. Cl.
CPC ............... *A61M 2205/3303* (2013.01); *A61M 2205/3365* (2013.01); *A61M 2230/06* (2013.01); *A61M 2230/201* (2013.01); *A61M 2230/208* (2013.01); *A61M 2230/50* (2013.01); *A61M 2230/63* (2013.01)

(58) Field of Classification Search
CPC ..... A61B 5/746; A61B 5/0004; A61B 5/0024; A61B 5/1486; A61B 5/7246; A61B 5/7475; A61B 2560/0247; A61B 2560/0252; A61B 2560/0276; A61B 2560/0475; A61B 2562/0247; A61B 5/01; A61B 5/053; A61B 5/1118; A61B 5/14542; A61B 5/14546; A61B 5/1473; A61B 5/4833; A61B 5/4839; A61B 5/4848; A61B 5/4866; A61B 5/6826; A61B 5/7203; A61B 5/7221; A61B 5/7275; A61B 5/7278; A61B 5/7282; A61B 5/0095; A61B 5/1451; A61B 5/1455; A61B 5/6816; A61B 5/6824; A61B 5/6838; A61M 5/1723; A61M 2230/201; A61M 1/1609; A61M 1/34; A61M 1/342; A61M 1/3434; A61M 1/3437; A61M 1/3458; A61M 2205/3584; A61M 2205/3592; A61M 2205/50; A61M 2205/52; A61M 5/14276; B01D 61/32; C12Q 1/54; G16Z 99/00; G01N 2021/1708; G01N 21/1702; G01N 2201/0612; G01N 2201/08
USPC ......................... 340/825.19, 5.52, 5.82, 7.55, 340/286.07–286.09, 691.6, 539.22, 539.12
See application file for complete search history.

(56) References Cited

U.S. PATENT DOCUMENTS

| | | | | |
|---|---|---|---|---|
| 6,403,944 | B1* | 6/2002 | MacKenzie | A61B 5/0095 |
| | | | | 250/214.1 |
| 6,740,072 | B2* | 5/2004 | Starkweather | G16H 20/17 |
| | | | | 604/504 |
| 6,827,702 | B2* | 12/2004 | Lebel | G16H 40/67 |
| | | | | 604/67 |
| 7,299,082 | B2* | 11/2007 | Feldman | A61B 5/14532 |
| | | | | 600/309 |
| 7,722,535 | B2* | 5/2010 | Randlov | A61B 5/4872 |
| | | | | 600/306 |
| 7,811,246 | B2 | 10/2010 | Koops | |
| 8,961,416 | B2* | 2/2015 | Siddiqui | G16H 40/67 |
| | | | | 600/365 |
| 10,226,562 | B2* | 3/2019 | Schulte | A61M 1/1609 |
| 2003/0036683 | A1 | 2/2003 | Kehr et al. | |
| 2003/0208133 | A1* | 11/2003 | Mault | A61B 5/097 |
| | | | | 600/532 |
| 2005/0038328 | A1* | 2/2005 | Stoehrer | A61B 5/205 |
| | | | | 600/301 |
| 2010/0063438 | A1* | 3/2010 | Bengtsson | A61M 5/14248 |
| | | | | 604/66 |
| 2010/0268043 | A1 | 10/2010 | Yodfat et al. | |
| 2013/0226079 | A1* | 8/2013 | Pesach | G16H 20/10 |
| | | | | 604/66 |
| 2013/0345664 | A1* | 12/2013 | Beck | A61M 5/1723 |
| | | | | 604/504 |
| 2014/0221966 | A1 | 8/2014 | Buckingham et al. | |
| 2015/0011970 | A1 | 1/2015 | Kamen et al. | |
| 2015/0119667 | A1 | 4/2015 | Reihman et al. | |

* cited by examiner

APPARATUS FOR REGULATING THE CONCENTRATION OF GLUCOSE IN THE BLOOD OF A PERSON

CROSS-REFERENCE TO RELATED APPLICATIONS

This application is the United States national phase of International Application No. PCT/EP2017/080830 filed Nov. 29, 2017, and claims priority to European Patent Application No. 16201413.8 filed Nov. 30, 2016, the disclosures of which are hereby incorporated by reference in their entirety.

BACKGROUND OF THE INVENTION

The invention relates to an apparatus for regulating the concentration of glucose in the blood of a person. In particular the invention relates to such an apparatus, comprising:
- at least one glucose sensor that is arranged to measure the glucose concentration of the person, for example in the interstitial fluid or blood;
- a pump means for selectively introducing at least one substance influencing the blood glucose levels into the body of the person, for instance by means of at least one cannula or catheter to be inserted into the body of said person, and
- a control means for controlling said at least one substance influencing the blood glucose levels to be introduced to the person based on data received from said glucose sensor.

Such an apparatus is known per se. For example, such an apparatus is known from the international patent application WO2007/049961.

SUMMARY OF THE INVENTION

It is an object of the invention to improve apparatus disclosed in WO2007/049961.

This object is achieved by providing an apparatus of the type described herein that is characterized by at least one further sensor that is arranged to monitor a further characteristic of the person.

Monitoring said further characteristic of the person can be used for more accurately determining a type and/or an amount of the substance that influences blood glucose levels to be provided to the person. Additionally or alternatively, the further characteristic can be used to adapt the behaviour and/or settings of the apparatus.

Said substance that may influence the blood glucose level may be any suitable substance. Said substance may influence the blood glucose level either directly or indirectly. Said substance may for example be insulin, glucagon or another hormone, or glucose.

Said further sensor may be any type of sensor. In particular said further sensor may be any sensor providing data that is indicative for the responsiveness of the person to said at least one substance influencing the blood glucose levels and may therefore require an adaption of the amount of substance influencing blood glucose levels to be provided to that person. The amount of substance influencing blood glucose levels to be provided to that person may be calculated using an algorithm taking into account both the glucose concentration of the person as measured by the glucose sensor and the data that is indicative for the responsiveness of the person to said at least one substance influencing blood glucose levels as measured by said at least one further sensor.

For example, the physical or mental activity of the person may influence the responsiveness of the person to said at least one substance influencing blood glucose levels and may therefore require an adaption of the amount of this substance to be provided to that person. The amount of blood glucose level influencing substance to be provided to that person may be calculated using an algorithm taking into account both the glucose concentration of the person as measured by the glucose sensor and the physical and/or mental activity as measured directly or indirectly by said further sensor.

Said further sensor may therefore in particular be a sensor for measuring data indicative for the physical and/or mental activity of the person.

In an embodiment of the apparatus according to the invention said control means for controlling said at least one substance influencing the blood glucose levels to be introduced to the person may also be based on data received from said at least one further sensor.

Said control means may in particular comprise a controller, more in particular for example a processor.

In another embodiment of the apparatus according to the invention said at least one further sensor is an accelerometer.

With use of such an accelerometer various data about the person may be provided. The accelerometer may for example provide data on the type of physical activity of the person and/or the intensity thereof and/or the position and/or orientation of the body.

In another embodiment of the apparatus according to the invention said at least one further sensor is a heart rate sensor arranged to measure the heart rate of the person.

If a person is physically or mentally active the heart rate of the person may be relatively high, and vice versa. As such, the heart rate of the person may be indicative for the mental and/or physical activity of the person, such that the behaviour of the apparatus for regulating the glucose concentration in the body of a person may be adapted thereto.

In another embodiment of the apparatus according to the invention said at least one further sensor is a temperature sensor arranged to measure the body temperature of the person.

If a person is physically or mentally active and starts sweating, the body temperature of the person may decrease, or vice versa. As such, the body temperature may be indicative for the mental and/or physical activity of the person, such that the behaviour of the apparatus for regulating the glucose concentration in the body of a person may be adapted thereto.

In yet another embodiment, the at least one further sensor may comprise a pH sensor arranged to measure the acidity of the blood of the person. A lack of insulin may lead to acidification of the body, which may be detected by measuring the pH of the blood.

In another embodiment of the apparatus the at least one further sensor may comprises a ketone sensor which is arranged to detect ketone bodies in the body of the person. Such ketone bodies are formed when there is a lack of insulin, so that the amount of ketone bodies may serve as an indication e.g. that the person is not responding to an insulin injection.

It is also conceivable that the at least one further sensor comprises a GPS receiver arranged to detect the location of the person. Although such a GPS receiver can obviously not monitor any bodily characteristic, it does provide information about movement of the person. GPS data allow a determination to be made if the person is exercising, e.g. walking, running or cycling, or if the person is driving around in a car. This information may be useful e.g. in determining a dosage regimen for insulin, glucagon or glucose.

If the at least one further sensor comprises a skin resistance sensor arranged to measure galvanic resistance of the skin of the person, an indication is provided of the amount of perspiration, since perspiration leads to a change in the galvanic resistance. Perspiration may either be an indication of physical exercise, or an indication of a decrease in the blood glucose level. When the skin resistance sensor is combined with an accelerometer or a GPS receiver, the system can distinguish between perspiration due to physical exercise, which will involve continuous movement or acceleration, and perspiration due to falling blood glucose levels, which may occur even when the person is at rest.

As indicated above, the output of said at least one further sensor may be used to adapt the behaviour and/or settings of the apparatus for regulating the glucose concentration in the blood of a person. For instance, if the output of the further sensor indicates that the person is asleep, then the volume of an alarm function of the apparatus may be temporarily reduced and/or an alarm may temporarily not be provided and/or a display of the apparatus may be dimmed and/or messages of low priority may not be shown and/or said apparatus may check and if necessary adapt its settings. It is noted that said apparatus may in particular be arranged such that it does not provide the alarm or reduces the volume of the alarm function only when the situation is not critical. Said apparatus may return to its normal settings when said person wakes up.

For example said accelerometer may be used to determine if said person is asleep, because the orientation of said person may be determined thereby, by means of which lying down may be distinguished from standing still.

In another embodiment of the apparatus according to the invention said apparatus comprises a second glucose sensor that is arranged to measure the concentration of glucose in the body of the person.

An advantage of providing two glucose sensors is that the measurements may continue if one fails, i.e. for redundancy. Additionally or alternatively, the measurements of the two glucose sensors may be compared to verify the quality of the measurements, or they may be combined to generate an average value. In any event the second glucose sensor is important for the quality and continuity of the monitoring.

In another embodiment of the apparatus according to the invention said apparatus comprises at least two further sensors.

Said at least two further sensors may be any type of sensor, for example any type of sensor as described above and/or in the claims. In particular any of said further sensors may be chosen from the group comprising an accelerometer, a heart rate sensor, a temperature sensor, a pH sensor, a ketone sensor, a skin resistance sensor and a GPS receiver Said at least two further sensors may be the same or different sensors.

Said at least two further sensors may be provided for redundancy or for improving the quality of the measurements of the physical and/or mental activity.

For example, when two accelerometers are provided, the type of physical activity performed by the person may be more accurately determined. The two further sensors may for example be applied to different parts of the body of the person.

It is noted that for example cycling is a difficult activity to distinguish from other activities. With use of two accelerometers which measure an acceleration of the body of the person at two different positions thereof, it is possible to determine whether the person is cycling or performing another activity.

Any of said glucose sensor(s) and/or said further sensor(s) may be arranged such that it may be attached to the body of the person.

Such a glucose sensor and/or further sensor that is attached to the body of the person may provide more accurate information compared to a sensor that is not attached to said person.

For example, any of said glucose sensor(s) and/or further sensor(s) may be attached to the skin of the person by using an adhesive such that the glucose and/or further sensor sticks to the skin of the person, for example as a plaster.

Alternatively, any of said glucose sensor(s) and/or further sensor(s) may be an invasive sensor. In such an embodiment that glucose and/or further sensor may be in contact with the bodily fluid or the blood of a patient.

Said measurement may be performed either through the skin, subcutaneously, or directly in the blood of the patient.

Said apparatus may be any type of apparatus for regulating the concentration of glucose in the blood of a person such as, but not limited thereto, an artificial pancreas, a bionic pancreas, a closed loop glucose control system, a low glucose suspend system or a hybrid closed loop control system, An advantage of such apparatuses is that they may automatically calculate the required amount of blood glucose influencing substances to be injected to achieve stable blood glucose levels. These substances may be introduced in the body with or without intervention of the user.

Such apparatuses may make use of an algorithm which incorporates an adjustable curve corresponding to the amount of blood glucose influencing substances introduced into the body of the person and the nominal concentration of the glucose in the body of the person as a reaction thereto. The data provided by said (second) further sensor may be used in this algorithm or adjustable curve.

In particular the apparatus may be the apparatus described WO2007/049961 which is incorporated herein in its entirety by reference.

In another embodiment of the apparatus according to the invention the pump means comprise two pumps, one for introducing substances to increase the blood glucose levels of the person and one for introducing substances to decrease the blood glucose levels of the person, and an individual cannula or catheter is added to each pump.

In another embodiment of the apparatus according to the invention the pump means comprise two pumps, one for introducing substances to increase the blood glucose levels of the person and one for introducing substances to decrease the blood glucose levels of the person, and one shared cannula or catheter with two passages is added to the two pumps, wherein one serves for transport of substances to increase the blood glucose levels of the person and one for transport of substances to decrease the blood glucose levels of the person.

In an embodiment of the apparatus according to the invention any of the (shared) cannula(s) or catheter(s) comprise(s) said glucose sensor(s) and/or said at least one further sensor(s). For example, said glucose sensor(s) and/or said further sensor(s) may be carried by, or may be part of any of said (shared) cannula(s) or catheter(s).

In yet another embodiment of the apparatus according to the invention, the apparatus comprises a second control means.

Said second control means may be arranged to monitor said control means, which control means are referred to hereafter as the first control means.

An advantage of providing two control means is that a dual system is provided, which may be safer than providing only one control means.

Said second control means may in particular be a controller, more in particular for example a processor.

Said second control means and said first control means may be made by different suppliers and/or may use different software.

If said first and second control means are made by different suppliers and/or use different software, errors resulting from manufacturing and/or software codes may be detected as this may result in a different calculated amounts of substance influencing blood glucose levels to be provided to a user by the two control means.

Both of said second control means and said first control means may be arranged to independently from the other control means process the data obtained by the same glucose sensor, or optionally by a respective glucose sensor out of two glucose sensors, and the same at least one further sensor, or optionally by a respective further sensor out of at least two further sensors, and to determine the amount of substance influencing blood glucose levels to be provided to a user of the apparatus. The amount of substance influencing blood glucose levels to be provided to the user may for example be calculated using said algorithm taking into account both the glucose concentration of the person as measured by the at least one glucose sensor and the data that is indicative for the responsiveness of the person to said at least one substance influencing blood glucose levels as measured by said at least one further sensor.

Only said first control means may be arranged to control said pump means for selectively introducing at least one substance influencing the blood glucose levels into the body of the person. The amount of substance influencing blood glucose levels to be provided to the person as determined by the second control means may only be used for monitoring and/or checking the function of the first control means, and in particular for checking if the amount of substance to be supplied determined by the first control means is at least almost the same as the amount determined by the second control means. For example, if both the first control means and the second control means determine the same amount, or the amounts determined thereby differ maximally by a predetermined maximum difference value or percentage, the first control means may be arranged to control said pump means for selectively introducing the amount determined by the first control means. If however the first control means and the second control means determine a different amount, or if the amounts determined thereby differ more than said predetermined maximum difference value or percentage, the apparatus may be arranged to compute a difference amount of substance to be supplied based on both the amount determined by the first control means and the amount determined by the second control means. Such a difference amount may for example be an amount that lies between the amount determined by the first control means and the amount determined by the second control means, i.e. an average amount. Otherwise, if the first control means and the second control means determine a different amount, or if the amounts determined thereby differ more than said predetermined maximum difference value or percentage, or if the first control means determines a higher amount of substance to be supplied to the person than said second control means, the apparatus may be arranged to provide a warning signal to the user of the apparatus. In particular, the situation that the first control means calculates a higher amount of substance to be supplied to the person than said second control means may result in the apparatus providing a warning signal, because this may imply the risk of introducing an overdose of substance to the person. Together with providing the warning signal, the apparatus may lock and/or stop introducing the substance to the person until the device is checked and/or repaired.

Said predetermined maximum difference value may for example be 0 if both control means determine the amount of substance to be supplied based on the same input. Said predetermined maximum difference percentage may for example be 10% if each control means determines the amount of substance to be supplied based on the different input, for example obtained by different sensors.

Alternatively or additionally the second control means may be arranged to take over the control of the pump means from the first control means, for example upon a user deciding to input such instructions after receiving a said warning signal which may be applied if the first control means and the second control means determine a different amount, or if the amounts determined thereby differ more than said predetermined maximum difference value or percentage, or if the first control means determines a larger amount of substance to be supplied to the person than said second control means, and if the user determines that the amount determined by the first control means is incorrect and the amount determined by the second control means is correct.

If multiple glucose sensors and/or further sensors are provided, the respective glucose sensor and/or respective further sensor(s) used by each control means may change over time. The algorithm provided may be arranged to determine which sensor out of same type sensors, i.e. for example out of two glucose sensors or out of two same type further sensors, is most accurate at a certain time. The first control means, which first control means control the pump means, may use the data provided by the most accurate sensor of that time, and the second control means may use the data provided by the other sensor in order to check the calculations made by the first control means.

Alternatively or additionally the second control means may check the amount of substance influencing blood glucose levels that is actually introduced into the person. For example, the number of turns of a motor of the pump means may be indicative of the amount of substance introduced. If the amount of substance that is actually introduced into the person by the first control means and pump means as checked by the second control means differs from the amount that was determined, optionally only when the difference is larger than a predetermined difference value or percentage, the apparatus may be arranged to provide a warning signal to the user of the apparatus. Together with providing the warning signal, the apparatus may lock and/or stop introducing the substance to the person until the device is checked and/or repaired.

Advantageously said first and second control means may check each other on any desired parameter. For example, as may be described above, the first and second control means may check any one and more of:
  the measured glucose concentration of the person,
  the determined amount of substance influencing the blood glucose levels to be introduced to the person, the amount of substance influencing the blood glucose levels that is actually introduced to the person.

by the second control means, whether the first control means has initiated, activated or provided a warning signal.

The invention also relates to an apparatus for regulating the concentration of glucose in the blood of a person, said apparatus comprising:

at least one glucose sensor that is arranged to measure the glucose concentration of the person, for example in the interstitial fluid or blood;

a pump means for selectively introducing at least one substance influencing the blood glucose levels into the body of the person, for instance by means of at least one cannula or catheter to be inserted into the body of said person, and a first control means for controlling said at least one substance influencing the blood glucose levels to be introduced to the person based on data received from said glucose sensor, characterized in that said apparatus comprises a second control means arranged for independently from the first control means determining an amount of substance influencing the blood glucose levels to be introduced to the person based on data received from said glucose sensor or, optionally, a second glucose sensor.

An advantage of providing two control means is that a dual system is provided, which may be safer than providing only one control means.

Said first and/or second control means may in particular be a controller, more in particular for example a processor.

Said second control means and said first control means may be made by different suppliers and/or may use different software.

If said first and second control means are made by different suppliers and/or use different software, errors resulting from manufacturing and/or software codes may be detected as this may result in a different calculated amounts of substance influencing blood glucose levels to be provided to a user by the two control means.

Both of said second control means and said first control means may be arranged to independently from the other control means process the data obtained by said glucose sensor or, optionally, by a respective glucose sensor of the first and second glucose sensors to determine the amount of substance influencing blood glucose levels to be provided to a user of the apparatus. The amount of substance influencing blood glucose levels to be provided to the user may for example be calculated using said algorithm taking into account the glucose concentration of the person as measured by the glucose sensor and, optionally, the second glucose sensor.

Only said first control means may be arranged to control said pump means for selectively introducing at least one substance influencing the blood glucose levels into the body of the person. The amount of substance influencing blood glucose levels to be provided to the person as determined by the second control means may only be used for monitoring and/or checking the function of the first control means, and in particular for checking if the amount of substance to be supplied determined by the first control means is at least almost the same as the amount determined by the second control means. For example, if both the first control means and the second control means determine the same amount, or the amounts determined thereby differ maximally by a predetermined maximum difference value or percentage, the first control means may be arranged to control said pump means for selectively introducing the amount determined by the first control means. If however the first control means and the second control means determine a different amount, or if the amounts determined thereby differ more than said predetermined maximum difference value or percentage, the apparatus may be arranged to compute a difference amount of substance to be supplied based on both the amount determined by the first control means and the amount determined by the second control means. Such a difference amount may for example be an amount that lies between the amount determined by the first control means and the amount determined by the second control means, i.e. an average amount. Otherwise, if the first control means and the second control means determine a different amount, or if the amounts determined thereby differ more than said predetermined maximum difference value or percentage, or if the first control means determines a higher amount of substance to be supplied to the person than said second control means, the apparatus may be arranged to provide a warning signal to the user of the apparatus. In particular, the situation that the first control means calculates a higher amount of substance to be supplied to the person than said second control means may result in the device providing a warning signal, because this may imply the risk of introducing an overdose of substance to the person. Together with providing the warning signal, the device may lock and/or stop introducing the substance to the person until the device is checked and/or repaired.

Said predetermined maximum difference value may for example be 0 if both control means determine the amount of substance to be supplied based on the same input. Said predetermined maximum difference percentage may for example be 10% if each control means determines the amount of substance to be supplied based on the different input, for example obtained by different sensors.

Alternatively or additionally the second control means may be arranged to take over the control of the pump means from the first control means, for example upon a user deciding to input such instructions after receiving a said warning signal which may be applied if the first control means and the second control means determine a different amount, or if the amounts determined thereby differ more than said predetermined maximum difference value or percentage, or if the first control means determines a larger amount of substance to be supplied to the person than said second control means, and if the user determines that the amount determined by the first control means is incorrect and the amount determined by the second control means is correct.

Said first and second control means may use input from one and the same glucose sensor in order to determine the amount of substance to be supplied to the user.

Alternatively, said first and second control means may use input from different, respective glucose sensors in order to determine the amount of substance to be supplied to the user.

The respective glucose sensor used by each control means may change over time. The algorithm provided may be arranged to determine which glucose sensor out of the two glucose sensors is most accurate at a certain time. The first control means, which first control means control the pump means, may use the data provided by the most accurate sensor of that time, and the second control means may use the data provided by the other sensor in order to check the calculations made by the first control means.

Alternatively or additionally the second control means may check the amount of substance influencing blood glucose levels that is actually introduced into the person. For example, the number of turns of a motor of the pump means may be indicative of the amount of substance introduced. If the amount of substance that is actually introduced into the person by the first control means and pump means as checked by the second control means differs from the amount that was determined, optionally only when the difference is larger than a predetermined difference value or percentage, the apparatus may be arranged to provide a warning signal to the user of the apparatus. Together with providing the warning signal, the apparatus may lock and/or stop introducing the substance to the person until the device is checked and/or repaired.

Advantageously said first and second control means may check each other on any desired parameter. For example, as may be described above, the first and second control means may check any one and more of:
- the measured glucose concentration of the person,
- the determined amount of substance influencing the blood glucose levels to be introduced to the person,
- the amount of substance influencing the blood glucose levels that is actually introduced to the person, and
- by the second control means, whether the first control means has initiated, activated or provided a warning signal.

BRIEF DESCRIPTION OF THE DRAWINGS

The invention will be further elucidated with reference to a figure shown in a drawing in which.

DESCRIPTION OF THE INVENTION

Figure 1:
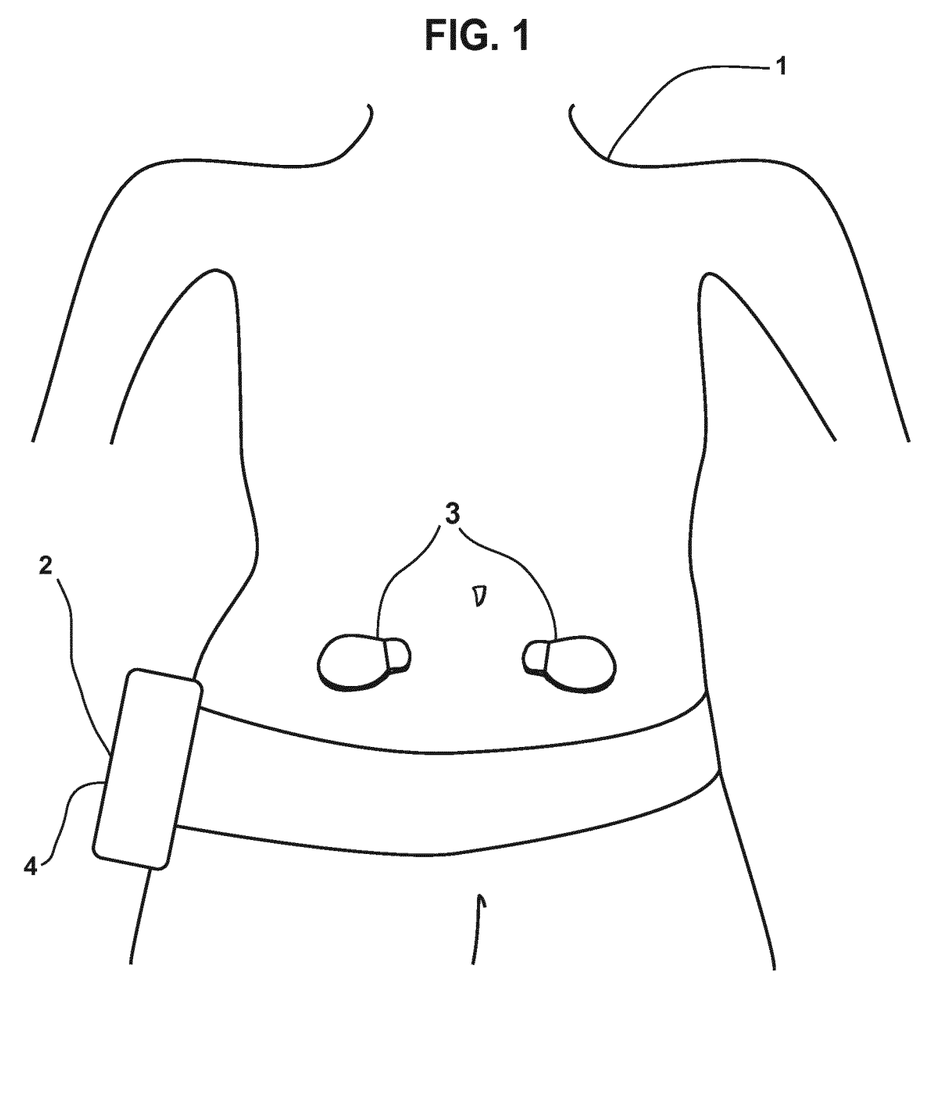
FIG. 1 schematically shows a person carrying an apparatus according to the invention.

FIG. 1 schematically shows a person 1 carrying an apparatus 2 for regulating the concentration of glucose in the blood of the person. In the illustrated embodiment the apparatus 2 comprises a system 9 of multiple sensor devices 3A, 3B, although the apparatus 2 could also comprise only a single sensor device 3. Each sensor device 3A, 3B is connected to a controller 10, which in turn is connected to a pump means 4, which serves to introduce substances influencing the blood glucose levels into the body of the person under control of the controller 10. The pump means 4 includes at least one pump 11 and at least one cannula or catheter 5 connected to the pump 11. In the illustrated embodiment the apparatus 2 comprises two pumps 11A, 11B, each connected to a respective cannula or catheter 5A, 5B.

Each of said sensor devices 3 comprises a glucose sensor 6 that is arranged to measure the concentration of glucose in the body of the person 1 and at least one further sensor 7 that is arranged to monitor a further characteristic of the person.

The further characteristic may be a bodily characteristic, for example the person's heart rate or the person's body temperature. Further bodily characteristics include the acidity of the person's blood, the presence of ketone bodies or the galvanic resistance of the person's skin. Accordingly, the further sensor 7 may be a heart rate sensor, a temperature sensor, a pH sensor, a ketone sensor or a skin resistance sensor, respectively.

Other characteristics, which are not related to the person's body, include the person's position, the speed with which the person moves or the person's acceleration. For monitoring or measuring these characteristics the further sensor 7 may be a GPS receiver or an accelerometer, respectively. The acceleration that is measured may be the acceleration of the person 1, which may be derived from the person's speed, which in turn may be derived from the person's position. However, the acceleration may also be an acceleration of a body part, which may be indicative of a particular type of physical activity, e.g. running or cycling. In that case typically an accelerometer is attached to the relevant body part.

In case of a sensor system 9 including multiple sensor devices 3A, 3B, the further sensors 7A, 7B may be different sensors, so that a greater number of characteristics can be monitored simultaneously.

Figure 2:
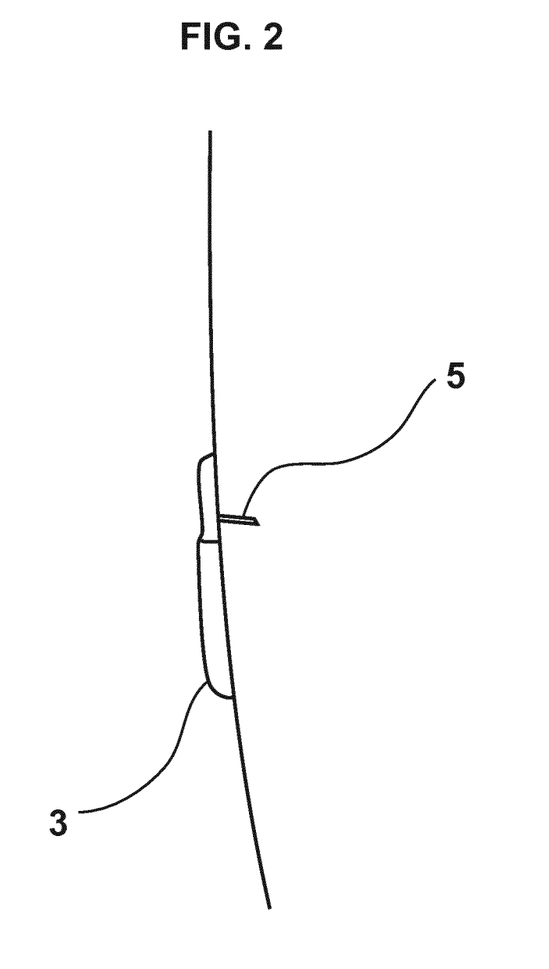
FIG. 2 is a cross section through a sensor device of the system of FIG. 1.

As is shown in FIG. 2, part of the apparatus 2 may be invasive and extend through the skin of the person 1. The invasive part of the apparatus may be the cannula or catheter 5 which serves for introducing blood glucose influencing substances into the body of the person 1. The cannula or catheter 5 may also serve for measuring the glucose concentration and/or for monitoring said further characteristic, if the further characteristic is a bodily characteristic. The two pumps 11A, 11B of the pump means 4 may serve for introducing different glucose influencing substances. Each cannula or catheter 5 may be one shared cannula or catheter with two passages, wherein both passages serve for different glucose influencing substance transport.

Instead of being integrated with the cannula or catheter 5 for introducing blood glucose influencing substances into the body of the person 1, the glucose sensors 6 and/or the further sensors 7 may also be separate therefrom. In particular when the further sensor 7 is arranged for monitoring a non-bodily characteristic, its location on the person's body may be spaced apart from the glucose sensor 6 and from the cannula or catheter 5. The glucose sensors 6 and the further sensors 7 are arranged to send output signals to the controller 10 by means of connections 8. These connections 8 may be wired or wireless communications channels.

Figure 4:
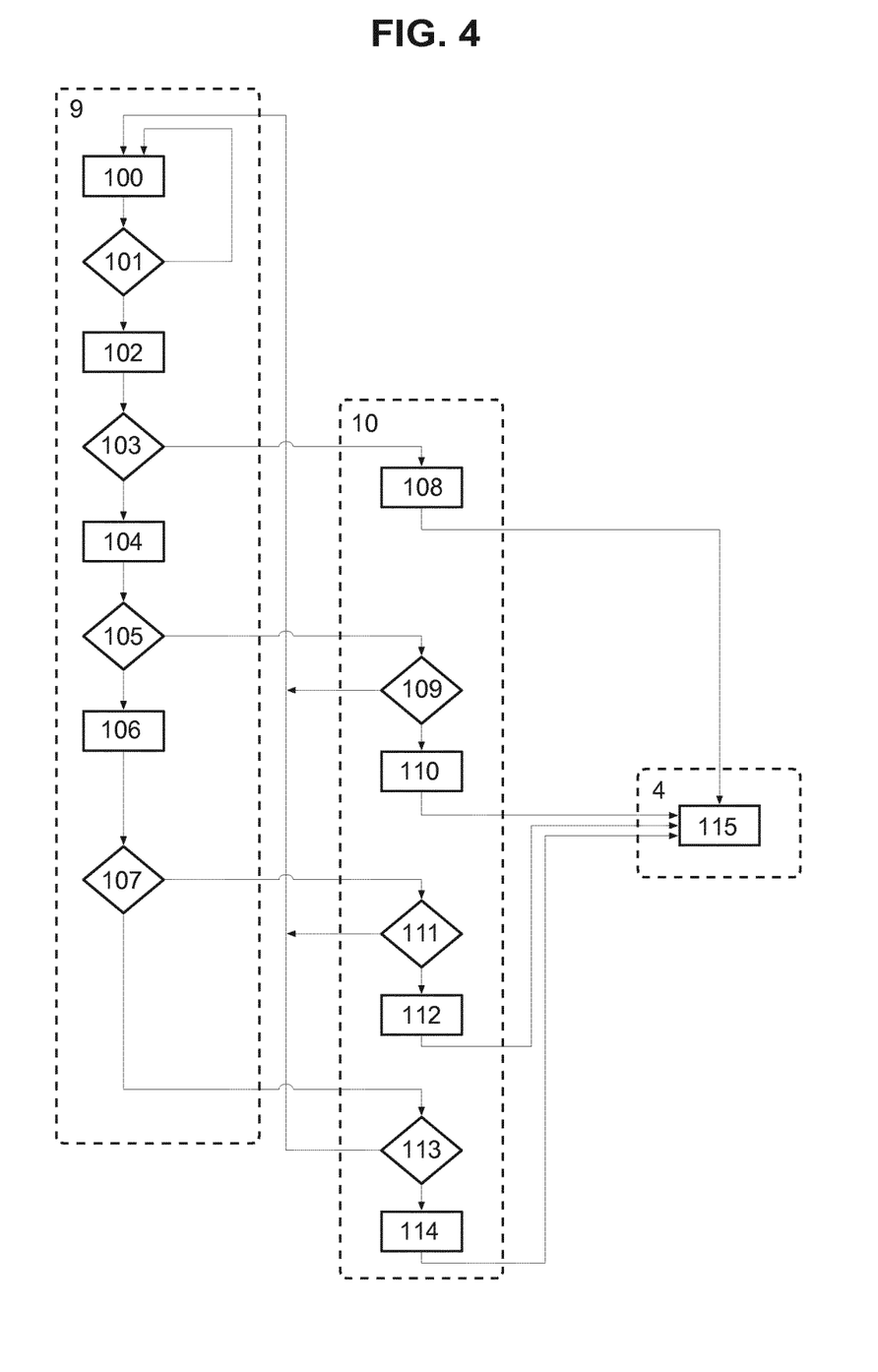
FIG. 4 is a flow chart showing how sensor outputs are used to control a supply of a blood glucose influencing substance to a person.

One way in which the apparatus 2 may be used to regulate the blood glucose level of the person is illustrated in FIG. 4. A sample is taken from a measurement by the first glucose sensor 6A (step 100). Then a determination is made if the sample is valid (step 101). This determination involves checking the measurement for noise and plausibility. If the sample cannot be validated, then the program returns to step 100 and a new sample taken by sensor 6A is selected.

If the measurement is validated, then a sample is taken from a measurement of a second sensor (step 102). In this embodiment the sample is a glucose measurement by the second glucose sensor 6B. Again, a determination is made whether or not the sample is valid.

If the sample is not validated, then the amount of blood glucose level influencing substance to be administered is calculated only on the basis of the measurement performed by the first glucose sensor (step 108). The calculated amount is then administered (step 115).

If the sample taken from the second glucose sensor 6B is found to be valid, then a sample is taken from a measurement by a third sensor 7A (step 104). In this embodiment the third sample is taken from a measurement of skin resistance by means of a galvanic resistance sensor 7A.

Again, a determination is made whether or not the third sample is valid (step 105).

If the sample is found not to be valid, then the samples from the first and second sensors 6A, 6B are compared (step 109). In case the values of these samples are found to be incompatible, the program returns to step 100 and a new sample from the glucose measurement sensor 6A is taken.

If, on the other hand, the samples are found to be compatible, then the amount of blood glucose level influencing substance to be administered is calculated on the basis of the measurements performed by the first and second glucose sensors 6A, 6B (step 110). In this embodiment an average value of the two glucose measurements is determined. Subsequently, the calculated amount of blood glucose level influencing substance is administered (step 115).

If the sample taken from the third sensor 7A is validated, then a sample is taken from a measurement by a fourth sensor 7B (step 106). In this embodiment, the fourth sample is taken from an acceleration measurement by means of an accelerometer 7B.

Once again, a determination is made whether or not the sample from the fourth sensor 7B is valid (step 107).

If the fourth sample is found not to be valid, then the samples from the first, second and third sensors 6A, 6B, 7A are compared (step 111). In case the values of these samples are found to be incompatible, the program returns to step 100 and a new sample from the glucose measurement sensor 6A is taken.

If the samples are found to be compatible, then the amount of blood glucose level influencing substance to be administered is calculated on the basis of the measurements performed by the first and second glucose sensors 6A, 6B and the skin resistance sensor 7A (step 112). In this embodiment the values of the two glucose measurements are compared to the galvanic skin resistance. If an increased level of perspiration is measured by the skin resistance sensor 7A while the blood glucose levels measured by the first and second glucose sensors 6A, 6B are low, this may be an indication of a hypoglycemia. This may lead to a higher or lower dose of the blood glucose level influencing substance being administered than would be done at normal level levels of perspiration. Then the calculated amount of blood glucose level influencing substance is administered (step 115).

In case the fourth sample is validated, then the samples from the first, second, third and fourth sensors 6A, 6B, 7A, 7B are compared (step 113). In case the values of these samples are found to be incompatible, the program returns to step 100 and a new sample from the glucose measurement sensor 6A is taken.

If the samples are found to be compatible, then the amount of blood glucose level influencing substance to be administered is calculated on the basis of the measurements performed by the first and second glucose sensors 6A, 6B, the skin resistance sensor 7A and the accelerometer 7B (step 114). In this embodiment the values of the two glucose measurements are compared to the galvanic skin resistance and the acceleration. If an increased level of perspiration is measured at low blood glucose levels while the person is physically active, as indicated by the accelerometer 7B, this may lead to a higher or lower dose of the blood glucose level influencing substance being administered than would be done if the person were sweating at low glucose levels and no physical activity. Then the calculated amount of blood glucose level influencing substance is administered (step 115).

Figure 3:
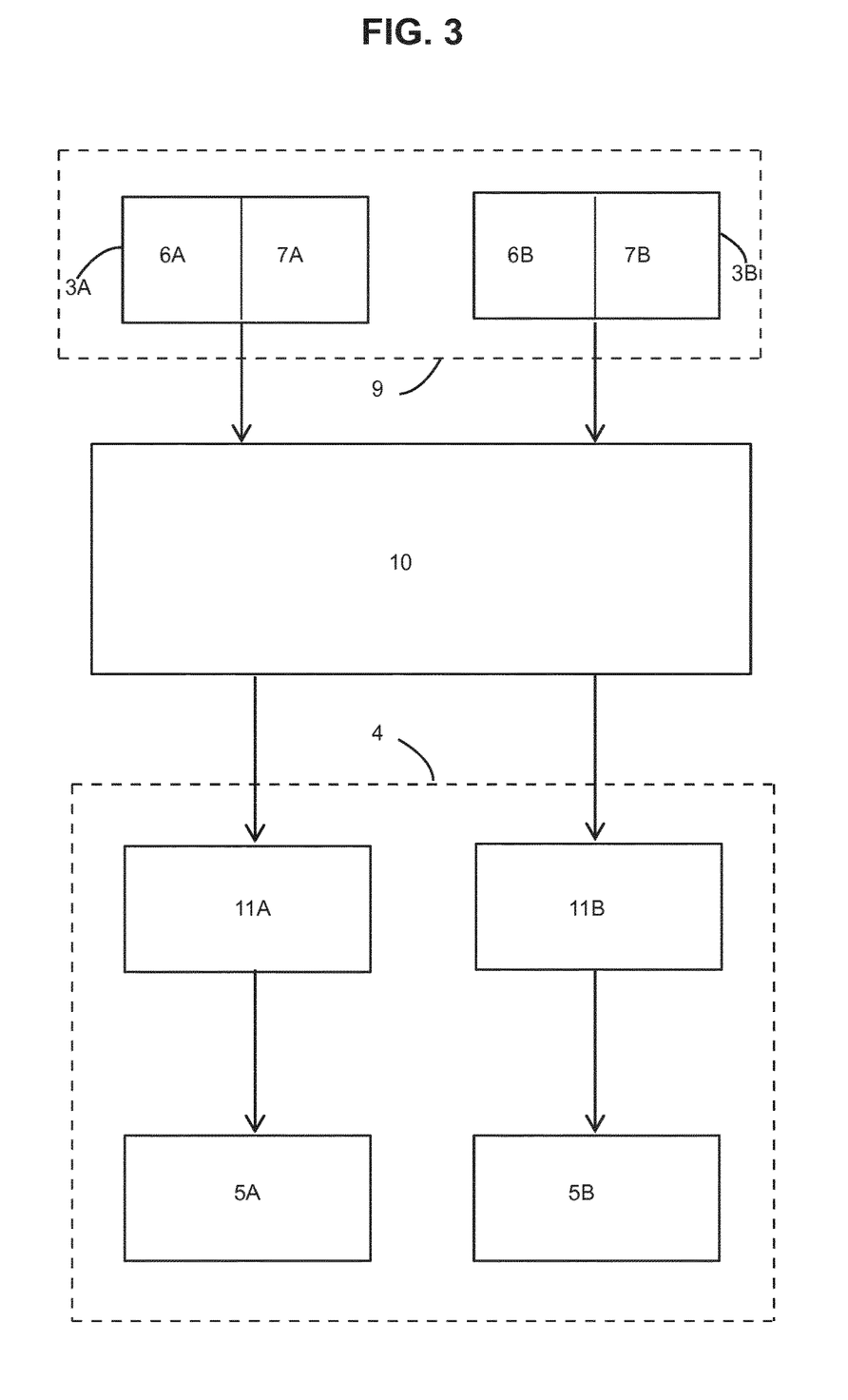
FIG. 3 is a schematic representation of the glucose concentration regulating apparatus of the invention.
Figure 5:
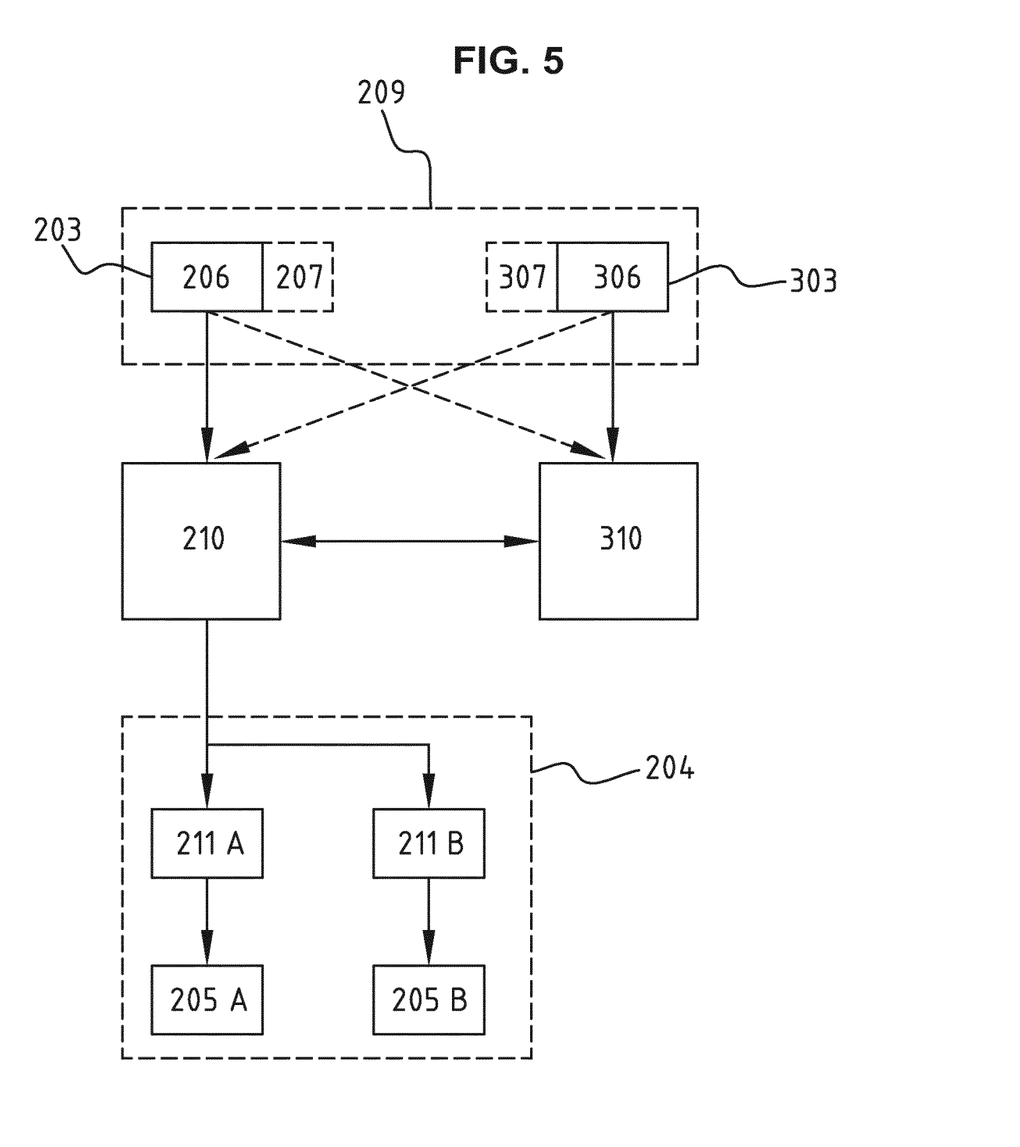
FIG. 5 is a schematic representation of an apparatus comprising two control means.

FIG. 5 shows an apparatus according to a further embodiment. Same elements are denoted by same reference numerals, increased by 200 or 300. Only the differences with the apparatus of FIGS. 1-3 is described here, for a further description the reader is referred to the description of FIGS. 1-3.

The apparatus 202 according the further embodiment comprises a first controller 210 and a second controller 310. The first controller 210 is connected to both sensor devices 206 and 306, and the second controller is connected to both sensor devices 206 and 306. In this embodiment, the first controller 210 is the only controller that is connected to pump means 204 for controlling the two pumps 211A, 211B thereof in such a manner that determined amounts of substances influencing the blood glucose levels are introduced into the body of the person via the respective cannula or catheter 205A, 205B. In this embodiment, the second controller 310 does not control any pump means, but only checks the functioning of the first controller 210, for example by checking the amounts of substances influencing the blood glucose levels to be introduced as determined by the first controller 210. In this embodiment, the first controller 210 uses the input of the sensor device 203, 303 that is, at that specific time, the most accurate of the two sensor devices 203, 303. In this embodiment the sensor devices 203, 303 each comprise only a glucose sensor 206, 207, but optionally a said at least one further sensor 207, 307 may be provided, as is indicated by the dashed lines. In this embodiment two sensor devices 203, 303 are provided, but optionally only one sensor device 203 may be provided, comprising said glucose sensor 206 and optionally a said at least one further sensor 207, wherein both controllers 210 and 310 use the input of said one sensor device 203.

In this embodiment, if the amounts of substances influencing the blood glucose levels to be introduced as determined by the first controller 210 are equal to the amounts determined by the second controller 310, or if the amounts as determined by the two controllers 210, 310 differ less than a predetermined maximum difference value or percentage, and in particular only when the amounts determined by the first controller 210 are smaller than the amounts determined by the second controller 310, the first controller 210 is arranged to control the pump means 204 to introduce the amounts calculated thereby. If however at least one of the amounts determined by the first controller 210 is different as the respective amount determined by the second controller 310, or if the at least one of the amounts as determined by the two controllers 210, 310 differs more than a predetermined maximum difference value or percentage, and in particular when the at least one amount determined by the first controller 210 is larger than the respective amount determined by the second controller 310, the apparatus 202 locks, stops introducing the substances into the person, and provides a warning signal to the person. This way it may be prevented that wrong amounts of substances are introduced to the person, and in particular that an overdoses is introduced.

Additionally or alternatively, the second controller 310 may check the amounts of substances influencing blood glucose levels that are actually introduced into the person by the pump means 204. For example, the number of turns of a motor of the pump means 204 may be indicative of the amount of substance introduced. If at least one of the amounts of substances that is actually introduced into the person by the first controller 210 and pump means 204 as checked by the second controller 310 differs from the amount that was determined, optionally only when the difference is larger than a predetermined difference value or percentage, the apparatus may be arranged to provide a warning signal to the user of the apparatus. Together with providing the warning signal, the apparatus may lock and/or stop introducing the substance to the person until the device is checked and/or repaired.

It is noted that the invention is not limited to the shown embodiments but also extends to variants within the scope of the appended claims or as described in the description.

The invention claimed is:

1. An apparatus for regulating the concentration of glucose in the blood of a person, comprising:
   at least one glucose sensor that is arranged to measure the glucose concentration of the person;
   a pump for selectively introducing at least one substance influencing the blood glucose levels into the body of the person, and
   a control for controlling said at least one substance influencing the blood glucose levels to be introduced to the person based on data received from said glucose sensor,
   wherein said apparatus comprises at least one further sensor that is arranged to monitor a further characteristic of the person, wherein the at least one further sensor monitors the further characteristic of the person by means other than a video image of the person,
   wherein said apparatus is arranged to determine, from the at least one further sensor, if said person is asleep or awake, and
   when said apparatus determines that said person is asleep, said apparatus is arranged to:
   temporarily reduce a volume of an alarm function of the apparatus; and/or
   temporarily not provide an alarm; and/or
   temporarily dim a display of the apparatus; and/or
   temporarily not show messages of low priority; and/or
   check and, if necessary, adapt settings of the apparatus.

2. The apparatus according to claim 1, wherein said at least one further sensor comprises an accelerometer.

3. The apparatus according to claim 1, wherein said at least one further sensor comprises a heart rate sensor arranged to measure a heart rate of the person.

4. The apparatus according to claim 1, wherein said at least one further sensor comprises a temperature sensor arranged to measure a body temperature of the person.

5. The apparatus according to claim 1, wherein said at least one further sensor comprises a pH sensor arranged to measure an acidity of the blood of the person.

6. The apparatus according to claim 1, wherein said at least one further sensor comprises a ketone sensor arranged to detect ketone bodies in the body of the person.

7. The apparatus according to claim 1, wherein said at least one further sensor comprises a GPS receiver arranged to detect a location of the person.

8. The apparatus according to claim 1, wherein said at least one further sensor comprises a skin resistance sensor arranged to measure galvanic resistance of the skin of the person.

9. The apparatus according to claim 1, wherein any of said at least one glucose sensor and/or said at least one further sensor is arranged to be attached to the body of the person.

10. The apparatus according to claim 9, wherein the at least one substance is introduced into the body by a cannula or a catheter to be inserted into the body, wherein the cannula or the catheter comprises any of said at least one glucose sensor and/or said at least one further sensor.

* * * * *